United States Patent
Gan et al.

(10) Patent No.: US 10,130,673 B2
(45) Date of Patent: *Nov. 20, 2018

(54) COMPOSITIONS COMPRISING KAKADU PLUM EXTRACT OR ACAI BERRY EXTRACT

(71) Applicant: Mary Kay Inc., Addison, TX (US)

(72) Inventors: David Gan, Southlake, TX (US); Michelle Hines, Hickory Creek, TX (US); Javier Aravena, Dallas, TX (US); Brian Jones, Flower Mound, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/283,633

(22) Filed: Oct. 3, 2016

(65) Prior Publication Data
US 2017/0020949 A1 Jan. 26, 2017

Related U.S. Application Data

(63) Continuation of application No. 13/759,822, filed on Feb. 5, 2013, which is a continuation of application No. 11/624,985, filed on Jan. 19, 2007.
(Continued)

(51) Int. Cl.
*A61K 36/889* (2006.01)
*A61K 36/185* (2006.01)
(Continued)

(52) U.S. Cl.
CPC ............ *A61K 36/889* (2013.01); *A61K 8/97* (2013.01); *A61K 9/0014* (2013.01); *A61K 9/06* (2013.01);
(Continued)

(58) Field of Classification Search
CPC .................................. A61K 8/97; A61K 36/889
See application file for complete search history.

(56) References Cited

U.S. PATENT DOCUMENTS

2,798,053 A 7/1957 Brown ............................ 521/38
3,755,560 A 8/1973 Dickert et al. ............. 514/772.6
(Continued)

FOREIGN PATENT DOCUMENTS

AU 2004203276 10/2005
AU 2005328670 9/2006
(Continued)

OTHER PUBLICATIONS

Strickland et al., J. Invest. Dermatol., 108: 763-768 (1997).*
(Continued)

*Primary Examiner* — Bethany P Barham
*Assistant Examiner* — Barbara S. Frazier
(74) *Attorney, Agent, or Firm* — Norton Rose Fulbright US LLP

(57) ABSTRACT

A method of reducing TNF-α production in human epidermal keratinocytes, the method comprising topically applying to skin in need thereof a composition comprising an effective amount of a liquid kakadu plum extract comprising kakadu plum fruit, alcohol, and butylene glycol to reduce TNF-α production in human epidermal keratinocytes of the skin, and an effective amount of a liquid acai berry extract comprising acai berry fruit, water, and alcohol to reduce TNF-α production in human epidermal keratinocytes of the skin.

6 Claims, 4 Drawing Sheets

Related U.S. Application Data

(60) Provisional application No. 60/760,977, filed on Jan. 20, 2006, provisional application No. 60/760,979, filed on Jan. 20, 2006, provisional application No. 60/760,103, filed on Jan. 19, 2006.

(51) Int. Cl.

| | | |
|---|---|---|
| *A61K 9/107* | (2006.01) | |
| *A61K 9/06* | (2006.01) | |
| *A61K 9/00* | (2006.01) | |
| *A61K 8/97* | (2017.01) | |
| *A61K 45/06* | (2006.01) | |
| *A61Q 19/02* | (2006.01) | |
| *A61Q 19/08* | (2006.01) | |

(52) U.S. Cl.
CPC ............ *A61K 9/107* (2013.01); *A61K 36/185* (2013.01); *A61K 45/06* (2013.01); *A61Q 19/02* (2013.01); *A61Q 19/08* (2013.01); *A61K 2800/522* (2013.01)

(56) References Cited

U.S. PATENT DOCUMENTS

| | | | |
|---|---|---|---|
| 4,421,769 A | 12/1983 | Dixon et al. | 514/772 |
| 4,509,949 A | 4/1985 | Huang et al. | 8/558 |
| 4,599,379 A | 7/1986 | Flesher et al. | 524/801 |
| 4,628,078 A | 12/1986 | Glover et al. | 526/303.1 |
| 4,835,206 A | 5/1989 | Farrar et al. | 524/457 |
| 4,849,484 A | 7/1989 | Heard | 525/221 |
| 5,011,681 A | 4/1991 | Ciotti et al. | 510/136 |
| 5,087,445 A | 2/1992 | Haffey et al. | 424/59 |
| 5,100,660 A | 3/1992 | Hawe et al. | 424/78.35 |
| 5,411,744 A | 5/1995 | Hill et al. | 424/450 |
| 5,470,874 A * | 11/1995 | Lerner | A61K 8/42 424/195.18 |
| 5,652,261 A | 7/1997 | Ismail | 514/168 |
| 5,720,963 A | 2/1998 | Smith | 424/401 |
| 6,054,296 A | 4/2000 | Bergstrom et al. | 435/69.3 |
| 6,068,842 A | 5/2000 | Bergstrom et al. | 424/184.1 |
| 6,090,586 A | 7/2000 | Bergstrom et al. | 435/69.3 |
| 6,113,914 A | 9/2000 | Lobet et al. | 424/234.1 |
| 6,126,951 A | 10/2000 | Fogel | 424/401 |
| 6,143,872 A | 11/2000 | Barbour et al. | 530/359 |
| 6,200,594 B1 | 3/2001 | Ernest et al. | 424/439 |
| 6,203,802 B1 | 3/2001 | Handjani et al. | 424/401 |
| 6,204,018 B1 | 3/2001 | Bergstrom et al. | 435/69.3 |
| 6,242,012 B1 | 6/2001 | Newmark et al. | 424/756 |
| 6,248,562 B1 | 6/2001 | Dunn et al. | 435/69.3 |
| 6,290,938 B1 | 9/2001 | Tanner et al. | 424/59 |
| 6,296,849 B1 | 10/2001 | Sadziene et al. | 424/141.1 |
| 6,300,101 B1 | 10/2001 | Sadziene et al. | 435/69.3 |
| 6,359,808 B1 | 3/2002 | Chen et al. | 365/185.21 |
| 6,387,398 B1 | 5/2002 | Vollhardt et al. | 424/450 |
| 6,495,126 B1 | 12/2002 | Schiltz | 424/78.02 |
| 6,509,017 B1 | 1/2003 | Bergstrom et al. | 424/184.1 |
| 6,524,626 B2 | 2/2003 | Chen | 424/728 |
| 6,610,838 B1 | 8/2003 | Bergstrom | 536/23.7 |
| 6,623,744 B2 | 9/2003 | Asmus et al. | 424/401 |
| 6,746,695 B1 | 6/2004 | Martin et al. | 424/734 |
| 6,780,442 B2 | 8/2004 | Bailey et al. | 424/732 |
| 6,814,970 B2 | 11/2004 | Sadziene et al. | 424/234.1 |
| 6,911,436 B2 | 6/2005 | Brown et al. | 514/54 |
| 7,175,862 B2 | 2/2007 | Pusateri et al. | 424/777 |
| 7,182,935 B2 | 2/2007 | Ribeiro de Nazare et al. | 424/9.71 |
| 7,384,654 B2 | 6/2008 | Menon et al. | 424/725 |
| 7,384,656 B2 | 6/2008 | Menon et al. | 424/739 |
| 2002/0022040 A1 | 2/2002 | Robinson et al. | 424/401 |
| 2003/0007939 A1 | 1/2003 | Murad | 424/61 |
| 2003/0095940 A1 | 5/2003 | Schiltz | 424/70.22 |
| 2003/0095959 A1 * | 5/2003 | Mayne | A61K 8/35 424/94.4 |
| 2003/0099727 A1 | 5/2003 | Tao et al. | 424/725 |
| 2003/0147977 A1 | 8/2003 | Goodman | 424/727 |
| 2003/0152544 A1 | 8/2003 | Chen | 424/74 |
| 2004/0022818 A1 | 2/2004 | Cho et al. | 424/401 |
| 2004/0043084 A1 | 3/2004 | Cioca et al. | 424/725 |
| 2004/0109905 A1 | 6/2004 | Bagchi | 424/732 |
| 2004/0116511 A1 | 6/2004 | Malik | 514/453 |
| 2004/0126351 A1 | 7/2004 | Hines et al. | 424/74 |
| 2004/0156818 A1 | 8/2004 | Lu et al. | 424/74 |
| 2004/0202726 A1 | 10/2004 | DeShay | 424/679 |
| 2005/0025737 A1 | 2/2005 | Sebagh | 424/74 |
| 2005/0048140 A1 | 3/2005 | Hines et al. | 424/725 |
| 2005/0048143 A1 | 3/2005 | McAnalley et al. | 424/729 |
| 2005/0087452 A1 | 4/2005 | McAnalley et al. | 205/777.5 |
| 2005/0123499 A1 | 6/2005 | Majmudar | 424/74 |
| 2005/0136141 A1 | 6/2005 | Stoner et al. | 424/765 |
| 2005/0163880 A1 | 7/2005 | Pusateri et al. | 424/777 |
| 2005/0196373 A1 | 9/2005 | Chen | 424/74 |
| 2005/0208564 A1 | 9/2005 | Ward et al. | 435/6 |
| 2005/0214413 A1 | 9/2005 | McAnalley et al. | 426/74 |
| 2005/0266018 A1 | 12/2005 | Boreyko et al. | 424/195.17 |
| 2006/0003353 A1 | 1/2006 | Ward et al. | 435/6 |
| 2006/0045896 A1 | 3/2006 | Morariu | 424/401 |
| 2006/0083795 A1 | 4/2006 | Shatkina et al. | 424/725 |
| 2006/0093685 A1 | 5/2006 | Mower et al. | 424/758 |
| 2006/0171938 A1 | 8/2006 | Stock et al. | 424/94.6 |
| 2006/0188590 A1 | 8/2006 | Ono | 424/756 |
| 2006/0210609 A1 | 9/2006 | Mower | 424/439 |
| 2006/0210621 A1 | 9/2006 | Mower | 424/451 |
| 2006/0210688 A1 | 9/2006 | Mower | 426/590 |
| 2006/0210692 A1 | 9/2006 | Mower | 426/618 |
| 2006/0210697 A1 | 9/2006 | Mower | 426/658 |
| 2006/0211652 A1 | 9/2006 | Mower | 514/54 |
| 2006/0216251 A1 | 9/2006 | Morariu | 424/59 |
| 2006/0251750 A1 | 11/2006 | Tabor | 424/757 |
| 2006/0275511 A1 | 12/2006 | Murdock et al. | 424/727 |
| 2007/0003685 A1 | 1/2007 | Wantanabe | 426/599 |
| 2007/0020286 A1 | 1/2007 | Dattwyler et al. | 424/190.1 |
| 2007/0020358 A1 | 1/2007 | Mower | 426/74 |
| 2007/0065396 A1 | 3/2007 | Morariu | 424/74 |
| 2007/0086972 A1 | 4/2007 | Birnbaum | 424/74 |
| 2007/0087957 A1 | 4/2007 | Kidron | 514/3 |
| 2007/0116838 A1 | 5/2007 | Prakash et al. | 426/548 |
| 2007/0141211 A1 | 6/2007 | Kolar et al. | 426/302 |
| 2007/0141223 A1 | 6/2007 | Moore et al. | 426/601 |
| 2007/0196298 A1 | 8/2007 | Kostick et al. | 424/63 |
| 2007/0202062 A1 | 8/2007 | Workman et al. | 424/66 |
| 2007/0207188 A1 | 9/2007 | Miller et al. | 424/440 |
| 2007/0248700 A1 | 10/2007 | Alberte et al. | 424/769 |
| 2007/0264401 A1 | 11/2007 | Taormina et al. | 426/532 |
| 2007/0269576 A1 | 11/2007 | Barton et al. | 426/599 |
| 2007/0275104 A1 | 11/2007 | Kornman et al. | 424/729 |
| 2007/0286908 A1 | 12/2007 | Clampitt | 424/680 |
| 2007/0292560 A1 | 12/2007 | Quan et al. | 426/3 |
| 2008/0044539 A1 | 2/2008 | Perlman et al. | 426/542 |
| 2008/0050472 A1 | 2/2008 | Heuer et al. | 426/72 |
| 2008/0057157 A1 | 3/2008 | Almeida et al. | 426/20 |
| 2008/0076823 A1 | 3/2008 | Watkins et al. | 514/560 |
| 2008/0305218 A1 | 12/2008 | Kahn | 426/91 |

FOREIGN PATENT DOCUMENTS

| | | |
|---|---|---|
| AU | 2006237559 | 10/2006 |
| AU | 2007231781 | 10/2008 |
| AU | 2008100919 | 10/2008 |
| BR | 0107103 | 9/2003 |
| BR | 0203076 | 6/2004 |
| JP | H08-059425 | 3/1996 |
| JP | 11-246336 | 9/1999 |
| JP | 2000-119161 | 4/2000 |
| JP | 2000-327525 | 11/2000 |
| JP | 2000-327549 | 11/2000 |
| JP | 2000-327550 | 11/2000 |
| JP | 2000-327552 | 11/2000 |
| JP | 2001-031558 | 2/2001 |
| JP | 2001-031580 | 2/2001 |
| JP | 3431383 | 5/2003 |
| KR | 2000-0050304 | 8/2000 |
| KR | 2004-0040557 | 5/2004 |
| KR | 2006-0002838 | 1/2006 |

(56) References Cited

FOREIGN PATENT DOCUMENTS

| | | |
|---|---|---|
| WO | WO 1995/35379 | 12/1985 |
| WO | WO 1993/08306 | 4/1993 |
| WO | WO 1996/024327 | 8/1996 |
| WO | WO 1996/40718 | 12/1996 |
| WO | WO 2000/78966 | 12/2000 |
| WO | WO 2003/022070 | 3/2003 |
| WO | WO 2003/027258 | 4/2003 |
| WO | WO 2003/075869 | 9/2003 |
| WO | WO 2003/088755 | 10/2003 |
| WO | WO 2004/084833 | 10/2004 |
| WO | WO 2005/022116 | 3/2005 |
| WO | WO 2005/072537 | 8/2005 |
| WO | WO 2005/074959 | 8/2005 |
| WO | WO 2006/026713 | 3/2006 |
| WO | WO 2006/045112 | 4/2006 |
| WO | WO 2006/055550 | 5/2006 |
| WO | WO 2006/074278 | 7/2006 |
| WO | WO 2006/102108 | 9/2006 |
| WO | WO 2006/119408 | 11/2006 |
| WO | WO 2006/121985 | 11/2006 |
| WO | WO 2006/130939 | 12/2006 |
| WO | WO 2007/029238 | 3/2007 |
| WO | WO 2007/053096 | 5/2007 |
| WO | WO 2007/053097 | 5/2007 |
| WO | WO 2007/053098 | 5/2007 |
| WO | WO 2007/054789 | 5/2007 |
| WO | WO 2007/061900 | 5/2007 |
| WO | WO 2007/062206 | 5/2007 |
| WO | WO 2007/084752 | 7/2007 |
| WO | WO 2007/084754 | 7/2007 |
| WO | WO 2007/084998 | 7/2007 |
| WO | WO 2007/090393 | 8/2007 |
| WO | WO 2007/095261 | 8/2007 |
| WO | WO 2007/098205 | 8/2007 |
| WO | WO 2007/102913 | 9/2007 |
| WO | WO 2007/102915 | 9/2007 |
| WO | WO 2007/106473 | 9/2007 |
| WO | WO 2007/109600 | 9/2007 |
| WO | WO 2007/109884 | 10/2007 |
| WO | WO 2007/115382 | 10/2007 |
| WO | WO 2007/131106 | 11/2007 |
| WO | WO 2007/133272 | 11/2007 |
| WO | WO 2007/133721 | 11/2007 |
| WO | WO 2007/137958 | 12/2007 |
| WO | WO 2007/140022 | 12/2007 |
| WO | WO 2008/008333 | 1/2008 |
| WO | WO 2008/009084 | 1/2008 |
| WO | WO 2008/018043 | 2/2008 |
| WO | WO 2008/028112 | 3/2008 |

OTHER PUBLICATIONS

"Beraca launches range of rainforest-sourced actives," Breaking News on Cosmetics Formulation & Packaging in North America, Jun. 9, 2005, retrieved on Nov. 11, 2010 from: http://www.cosmeticdesign.com/news/ng.asp?id=60570-rainforest-brazil-active.
"Berry good berry," People, Jan. 30, 2006.
"Cream Hair Colors," manufactured by Surya Nature, Apr. 2004.
"Daily Skin Shield Protective Moisture Lotion," manufactured by Unilever, Aug. 2006.
"Extract", Dictionary.pdf, p. 2/6 n. 11 and 12 accessed Aug. 3, 2016.
"Hair Mask," manufactured by Vedic Hindus, Jan. 2006.
"Kakadum Plum: Australian Patent Applications, Question 1172" The Senate Questions on Notice, Parliamentary Debates, Commonwealth of Australia, Mar. 10, 2009.
"Plantogen Anti Aging Cream Cleanser 5.1oz Beauty Cosmetics by Plantogen," available online at http://www.abs-sunglasses.com/pd-chanel-gucci-tiffany-glasses.aspx?pN=Plantogen_Anti_Aging_Cream_Cleanser_5_1oz&cN=Plantogen_Beauty_Cosmetics&pID=21049, accessed on Jul. 8, 2010. Copyright 2005.
"Red Earth gains award," The Sydney Morning Herald, [Sydney] Oct. 22, 1997, Late Edition, Illawarra Mercuy, p. 20.
"Shampoo for Color-Treated Hair," manufactured by Procter & Gamble, Jun. 2006.
27 CFR 21.22, Code of Federal Regulation, (2009) downloaded from http://www.gpo.gov/fdsys/granule/CFR-2009-title27-vol1/CFR-2009-title27-vol1-sec21-22/content-detail.html on Apr. 8, 2014.
Adore Beauty, "Balame Kakadu Plum Shave Foam", 2003, accessed at Internet Archive Wayback Machine, http://www.adorebeauty.com.au/cgi-bin/index.pl?BAKPSF, Aug. 2, 2016.
Baran et al., Textbook of Cosmetic Dermatology (2004), $3^{rd}$ Edition, pp. 725 and 728.
Brand et al., "The nutritional composition of Australian Aboriginal bushfoods," Food Technology in Australia, 35:293-298, 1982.
Cao et al., "Oxygen-radical absorbance capacity assay for antioxidants," Free Radic. Biol. Med., 14:303-311, 1993.
Coisson et al., "Euterpe oleracea juice as a functional pigment for yogurt," Food Research International 38:893-897, 2005.
Correspondence from Dr. Daniel Robinson to Mary Kay Inc., dated Mar. 2009.
Correspondence from Dr. Daniel Robinson to the IP Australia Staff, dated Oct. 14, 2009.
CTFA International Cosmetic Ingredient Dictionary, Tenth edition, 2004, Front matter only.
Del Pozo-Insfran et al., "Phytochemical composition and pigment stability of Acai (Euterpe oleracea Mart.)," J. Agric. Food Chem., 52:1539-1545, 2004.
Dimayuga et al., "SOD1 overexpression alters ROS production and reduces neurotoxic inflammatory signaling in microglial cells," J. Neuroimmunol., 182(1-2): 89-99 (Nov. 2006 epub).
Eurasian Office Action, issued in Eurasian Application No. 200801717, dated Jul. 1, 2009 (English Translation included).
Favacho et al., "Anti-inflammatory and antinociceptive activities of Euterpe oleracea oil," Brazilian Journal of Pharmacognosy, 21(1): 105-114 (2011).
Flick, Cosmetic Additives—An Industrial guide, William Andrew Publishing/Noyes 91991), p. 40.
Frank et al., "Regulation of Vascular Endothelial Growth Factor Expression in Cultured Keratinocytes: Implications for Normal and Impaired Wound Healing," Journal of Biological Chemistry, 270(21): 12607-12613. 1995.
Gorman et al., "An analysis of the use of plant products for commerce in remote Aboriginal communities of Northern Australia," Economic Botany, 60(4):362-373, 2006.
Hassimotto et al., "Antioxidant activity of dietary fruits, vegetables, and commercial frozen fruit pulps," J. Agric. Good. Chem. 53:2928-2935, 2005.
Horiguchi al., Journal of Agricultural and Food Chemistry, 59: 5595-5601 (2001).
Ikeda et al., "Suppressive Effect of Antioxidants on Intercellular Adhesion Molecule-1 (ICAM-1) Expression in Human Epidermal Keratinocytes," Journal of Investigative Dermatology 103:791-796 (1994).
Jagetia et al., "Evaluation of the effect of ascorbic acid treatment on wound healing in mice exposed to different doses of fractionated gamma radiation," Radiat. Res., 159:371-80, 2003 (Abstract).
Kreuter, "Possibilities of using nanoparticles as carriers for drugs and vaccines," J. Microencapsulation, 5:115-127, 1988.
Lichtenthaler et al., "Total oxidant scavenging capacities of Euterpe oleracea Mart. (Acai) fruits," Int. J. Food Sci. Nutr., 56:53-64, 2005.
Noratto et al., "Polyphenolics from Acai (Euterpe oleracea Mart.) and Red Muscadine Grape (Vitis rotundifolia) Protect Human Umbilical Vascular Endothelial Cells (HUVEC) from Glucose- and Lipopolysaccharide (LSP)-Induced Inflammation and Target MicroRNA-126," Journal of Agricultural and Food Chemistry, 59: 7999-8012 (2011).
Office Action issued in Korean Application No. 10-2008-7020280, dated Mar. 3, 2014. (English Translation).
Office Communication, issued in Australian Patent Application No. 2007205838, dated Oct. 21, 2009.
Office Communication, issued in Australian Patent Application No. 2007205838, dated Dec. 8, 2010.

(56) References Cited

OTHER PUBLICATIONS

Office Communication, issued in European Patent Application No. 07710236.6, dated Mar. 9, 2009.
Office Communication, issued in Taiwanese Patent Application No. 096102163, dated Apr. 7, 2011. (English translation).
Office Communication, issued in U.S. Appl. No. 11/624,985, dated Jul. 8, 2009.
Oram, "You're only as young as you feel, so best start stocking up on miracle creams and potent anti-aging lotion say Trudy Oram," *The Advertiser*, [Adelaide, S. Australia] 1 State Edition, Jan. 18, 2005, p. 36.
Packman and Gams, "Topical moisturizers: quantification of their effect on superficial facial lines," *J. Soc. Cos. Chem.*, 29:70-90, 1978.
Palliardi, "Tried & Tested," *Sunday Herald Sun*, [Melbourne], First Edition, Sep. 8, 2002, p. Z.32.
PCT International Search Report and Written Opinion, issued in International Application No. PCT/US 07/60792, dated Oct. 2, 2007.
Remington's Pharmaceutical Sciences, 18th Ed. Mack Printing Company, 1289-1329, 1990.
Robinson, "Guest article: The biological patent predicament. Traditional knowledge and biological product derivative patents: Benefit-sharing and patent issues relating to Camu Camu, Kakadu Plum and Acai Plant Extracts," United Nations University, Institute of Advanced Studies, Traditional Knowledge Initiative, available online at http://www.unutki.org/news.php?doc_id=174, published online Apr. 30, 2010.
Schauss et al., "Phytochemical and Nutrient Composition of the Freeze-Dried Amazonian Palm Berry, *Euterpe oleraceae* Mart. (Acai)" *Journal of Agricultural and Food Chemistry*, 54: 8598-8603 (2006).
Schiltz et al. "Retinoic acid induces cyclic changes in epidermal thickness and dermal collagen and glycosaminoglycan biosynthesis rates," *J. Investigative Dermatology*, 87:663-667, 1986.
Smith and Hong-Shum, Food Additives Data Book, Blackwell Publishing, 2003, pp. 145.
Stead, "Native magic," *The Sydney Morning Herald*, [Syndey] Mar. 14, 2000. Late Edition, Good Living, p. 20.
Taiwanese Search Report, issued in International Application No. 096102163, date of completion of search: Aug. 22, 2009 (English Translation).
Telang, "Vitamin C in Dermatology," *Indian Dermatology Online Journal* 4(2): 143-146. 2013.
The Journal of Investigative Dermatology, vol. 108, No. 3, pp. 302-306 (1997), Author: Tebbe et al.
Ward, "Beauty Spots," *The Sydney Morning Herald*, [Sydney] Jul. 21, 1997, Late Edition, Good Living, p. 8.
Whitehead et al., *Feasibility of Small Scale Commercial Native Plant Harvests by Indigenous Communities*, Rural Industries Research and Development Corporation (2006).
Woods, "A study of the intra-specific variations and commercial potential of *Terminalia ferdinandiana* exell (the Kakadu Plum)," M.S. Thesis. Northern Territory University, Darwin Jun. 1995.
Wynberg, "Rhetoric, Realism and Benefit Sharing: Use of Traditional Knowledge of *Hoodia* Species in the Development of an Appetite Suppressant," *Journal of World Intellectual Property*, 7(6):851-876, 2004.
Adore Beauty, "Baiame Kakadu Plum Aftershave Gel," 2003, <https://web.archive.org/web/200301 051 75433/https://www.adorebeauty. corn. au/cgi-bin/index. pl?BAKPSF,>.
Office Action issued in Canadian Patent Application No. 2,936,822, dated Jun. 7, 2017.
Jiao et al., "The Current Research and Development of Plant Flavonoids as Skin Care Facor in Field of Cosmetics," *Fine Chemical*, 2004, 21: 98-102. (English Translation).
Office Action issued in Chinese Patent Application No. 201410165509.1, dated Jul. 11, 2018.
Pang et al., "Women's Nutrition" People's Medical Publishing House, Oct. 1996, pp. 39-40. (English Translation).
Peng et al., "Application of Clinical Pharmacy in Nursing," Hubei Science and Technology Press, Feb. 1992, pp. 99-100 (English Translation).
Qui et al., "Manual for Pharmacist," People's Military Doctor Press, Feb. 1992, p. 544. (English Translation).
Zhan, Yixing "Green Fine Chemical Engineering—Preparing Methods for Natural Products," Science and Technology Document Press, May 2005, p. 617. (English Translation).
Zhang et al., "Manual of new drug preparation" Henan Science and Technology Press, Aug. 2001, (English Translation), p. 481.
Zhang et al., "National over the counter medicine family use guidelines" Guangdong People's Publishing House, 2000, pp. 196-197. (English Translation).
Rona et al., "The cosmetic treatment of wrinkles," *Journal of Cosmetic Dermatology*, 2004, 3:26-34.

\* cited by examiner

COMPOSITIONS COMPRISING KAKADU PLUM EXTRACT OR ACAI BERRY EXTRACT

CROSS REFERENCE TO RELATED APPLICATIONS

This application is a continuation of U.S. patent application Ser. No. 13/759,822 filed Feb. 5, 2013, which is a continuation of U.S. patent application Ser. No. 11/624,985, filed Jan. 19, 2007, which claims the benefit of U.S. Provisional Application Ser. No. 60/760,103, filed Jan. 19, 2006, U.S. Provisional Application Ser. No. 60/760,977, filed Jan. 20, 2006, and U.S. Provisional Application Ser. No. 60/760,979, filed Jan. 20, 2006. The contents of these applications are incorporated into the present application by reference.

BACKGROUND OF THE INVENTION

A. Field of the Invention

The present invention relates generally to compositions that can be used to improve the skin's visual appearance. In particular, the present invention concerns topical skin care compositions that include kakadu plum (*Terminalia ferdinandiana*) extract and/or acai berry extract (*Euterpe oleracea*).

B. Description of Related Art

With ageing, chronic exposure to adverse environmental factors, or malnutrition, the visual appearance, physical properties, and physiological functions of skin can change in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Several different approaches have been used to treat damaged skin caused by aging, environmental factors, chemicals, or malnutrition. One approach involves the use of specific agents to directly stimulate or inhibit selected biochemical targets. Examples include the use of retinoids to stimulate collagen and glycosaminoglycan synthesis by fibroblasts (Schiltz, et al., 1986). Another approach is to use agents or processes that stimulate the rate at which the epidermis replaces itself, a process known as epidermal cell renewal. Increases in epidermal cell renewal rates usually result from a more rapid rate of replication of epidermal basal cells, and can be caused by diverse stimuli such as chemical or physical injury, adverse environmental conditions, or direct stimulators of basal cell division.

Some examples of chemical injury include allergic or non-allergic contact irritation, pH extremes, or interaction of the stratum corneum with household or industrial chemicals or pollutants. Physical injury can include skin abrasion, friction (i.e. on the soles and heels of the feet), or removal of the stratum corneum by physical exfoliation (i.e. cosmetic masks) or by tape stripping. Agents that directly or indirectly stimulate basal cell division include retinoids and barrier disrupters. For example, U.S. Pat. No. 5,720,963 discloses that a combination of hydroxy acids, retinoids, and cerebrosides causes chronic injury to the stratum corneum and results in epidermal and dermal repair of the structurally-deteriorated skin. U.S. Pat. No. 6,495,126, for example, uses a combination of surfactants and chelating agents to stimulate an endogenous stratum corneum chymotryptic proteinase that causes a loosening of corneocytes, resulting in an increased rate of epidermal replacement and chronic anti-aging benefits. Adverse environmental exposures that can result in more rapid epidermal turnover rates include UVA, UVB, and IR radiation from the sun and cold coupled with low relative humidity (i.e. low dew point).

Several of the above methods have been shown to have various drawbacks, such as significant irritation to the skin or skin toxicity. In addition, most of these methods involve the invocation of chronic damage to the skin, which sets up repair mechanisms. For most of the existing treatments, there will be a period of time, up to several weeks or months, during which the skin becomes irritated and after which tolerance sets in and the symptoms of irritation may decrease and/or cease.

SUMMARY OF THE INVENTION

The present invention overcomes deficiencies in the art by providing compositions that can be used in skin treatment applications. The compositions of the present invention can include kakadu plum extract and/or acai berry extract. Further, as shown in the figures and examples (which are incorporated into this section by reference), the inventors have discovered that the combination of kakadu plum extract and acai berry extract produce synergistic and complimentary effects that are beneficial to skin.

In certain embodiments, the compositions are formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc.).

The compositions of the present invention can include from about 0.001% to about 50%, by weight, of kakadu plum extract and/or acai berry extract. It should be recognized, however, that the amount of kakadu plum extract and/or acai berry extract in a composition can be modified below, within, or above this range based on the desired results. Therefore, the amount of kakadu plum extract and/or acai berry extract can include less than 0.001%. In other aspects, the compositions can include 0.002, 0.003, 0.004 . . . 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 95, 96, 97, 98, 99%, or more or, or any range derivable therein, by weight or volume of kakadu plum extract and/or acai berry extract.

The compositions of the present invention can also be modified to have a desired oxygen radical absorbance capacity (ORAC) value. In certain non-limiting aspects, the compositions of the present invention, kakadu plum extract, and/or acai berry extract can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

In other non-limiting aspects of the present invention, the compositions can further include a vitamin, a mineral, an essential fatty acid, an amino acid, a flavonoid, and/or a protein, or a combination thereof. Non-limiting examples of vitamins include the B vitamins (e.g., B1, B2, B6, B12, niacin, folic acid, biotin, and pantothenic acid), vitamin C, vitamin D, vitamin E (e.g., tocopherol or tocopheryl acetate), vitamin A (e.g., palmitate, retinyl palmitate, or retinoic acid), and vitamin K. Non-limiting examples of minerals include iron, potassium, phosphorus, magnesium, manganese, selenium, and calcium. Non-limiting examples of essential fatty acids include Omega 3 (linolenic acid), Omega 6 (linoleic acid) and Omega 9 (oleic acid) essential fatty acid, or a combination thereof. Non-limiting examples of amino acids include essential amino acids (e.g., lysine, leucine, isoleucine, methionine, phenylalanine, threonine, tryptophan, valine, histidine, or arginine) and non-essential amino acids (e.g., serine, asparagine, glutamine, aspartic acid, glutamic acid, alanine, tyrosine, cysteine, glycine, or proline). Non-limiting examples of flavonoids include anthocyanin compounds (e.g., cyanidin-3-glucoside and cyanidin-3-rutinoside).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

The compositions can also include an essential oil. Non-limiting examples of essential oils are those described in the specification and those known to a person of ordinary skill in the art. Examples include sesame oil, macadamia nut oil, tea tree oil, evening primrose oil, Spanish sage oil, Spanish rosemary oil, Coriander oil, Thyme oil, or Pimento berries oil. In certain aspects, the compositions do not include a non-volatile oil. The compositions can include thickening agents an/or surfactants.

Also disclosed is a method of treating or preventing a skin condition comprising topical application of a composition comprising a high ORAC value, kakadu plum extract, and/or acai berry extract, wherein the topical application of the composition treats the skin condition. Non-limiting examples of skin conditions include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of lightening skin or evening skin tone comprising applying the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, or a freckle.

Also disclosed is a method of treating hyperpigmentation comprising applying the compositions of the present invention to the skin. The method can also comprise identifying a person in need of treating hyperpigmentation. Additional methods contemplated by the inventor include methods for reducing the appearance of an age spot, a skin discoloration, or a freckle, reducing or preventing the appearance of fine lines or wrinkles in skin, or increasing the firmness of skin.

Compositions comprising both kakadu plum extract and acai berry extract can produce synergistic effects. For example, the two extracts can work together synergistically to produce effects that exceed the effects of what would be expected if the extracts were used in separate compositions. Non-limiting synergistic effects include the reduction of internal or external oxidative damage, increased collagen production, reduction in inflammatory responses and the inhibition of melanogenesis.

Compositions comprising both kakadu plum extract and acai berry extract can also act in a complementary fashion. For example, kakadu plum extract can reduce inflammatory responses (e.g., the reduction of inflammatory cytokine production) by certain cytokines that are not reduced, or not as significantly reduced, by acai berry extract, and vice-versa.

Also contemplated are kits that includes the compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

It is contemplated that any embodiment discussed in this specification can be implemented with respect to any method or composition of the invention, and vice versa. Furthermore, compositions of the invention can be used to achieve methods of the invention.

A "non-volatile oil" includes those substance that will not evaporate at ordinary or room temperature.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as undissolved colloidal suspensions.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented below.

DESCRIPTION OF ILLUSTRATIVE EMBODIMENTS

Figure 1:
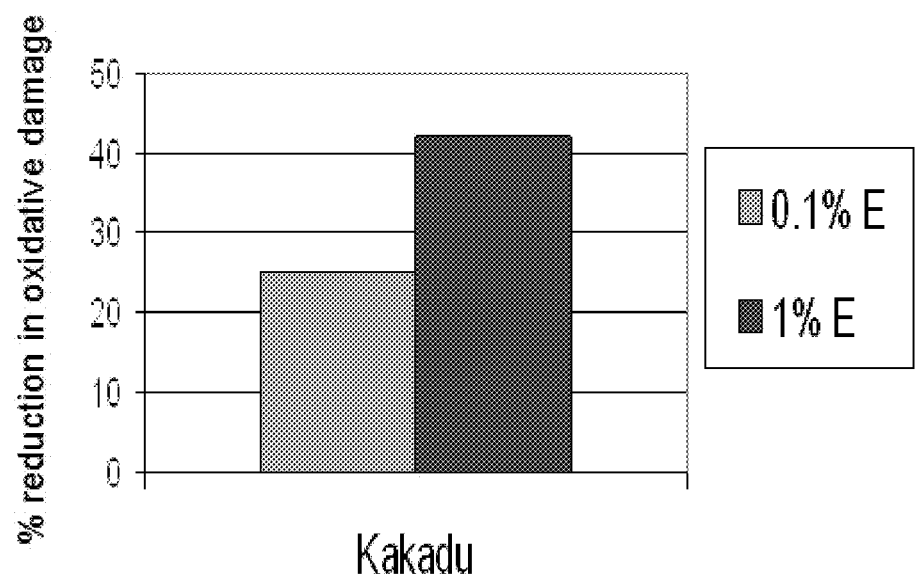
FIG. 1. Anti-oxidant effects of kakadu plum extract on human epidermal keratinocytes. E stands for external anti-oxidant according to the assay (External meaning is able to reduce oxidation that is introduced exogenously). 1% is volume per volume of the Kakadu diluted in water. The original liquid extract is listed at 20-30% W/W with 10-20% denatured alcohol and >50% 1,3 butylene glycol. A 10% stock of this extract was prepared by dilution is water (2-3% fruit extract) which was further diluted in the assay to 1.0% and 0.1% (0.2-0.3% and 0.02-0.03% kakadu fruit extract, based upon the amount in the original extract).

In today's image conscious society, people are continually looking for a product that can improve the visual appearance of their skin. Often times, aged skin, uneven skin tone, or skin damaged by environmental factors such as UV light, chronic sun exposure, environmental pollutants, chemicals, disease pathologies, or smoking, is associated with unattractive skin. Previous attempts to improve the visual appearance of skin has been shown to have various drawbacks such as skin irritation and prolonged recovery periods.

The present invention is an effective alternative to the use of retinoid compounds or other compositions and ingredients currently used to treat aged skin, environmentally-damaged skin, uneven skin tone, and other skin conditions. In one non-limiting aspect, the present invention can be used to improve the skin's visual appearance, physiological functions, clinical properties, or biophysical properties by providing kakadu plum extract and/or acai berry extract containing compositions. These and other aspect of the present invention are described in further detail below.

A. Kakadu Plum Extract

Kakadu plum (*Terminalia ferdinandiana*), also called Billygoat plum, Gubinge, or Murunga, is a flowing plant from the family *Combretacae*. Kakadu plum can be found in the tropical woodlands from northwestern Australia to eastern Arnhem Land. This fruit has a high vitamin C concentration, containing up to 4000 mg of vitamin C per 100 g of fruit. Kakadu plum also has a high ORAC value. Kakadu plum also includes phytochemicals such as gallic acid, ellagic acid, and related compounds. These phytochemicals have antioxidant properties that have been implicated in cancer inhibition. Gallic acid has an antibacterial, antiviral and antifungul activities and also shows anti-inflammatory, anti-tumor, anti-mutigenic and anti-bronchodilatory activities. Ellagic acid has anti-carcinogenic effects against a wide range of carcinogens in many human tissues.

Kakadu plum extract is available commercially and can also be isolated by a person of ordinary skill in the art using standard isolation techniques. For instance, kakadu plum can be disrupted by mechanical means which results in a puree. The puree is then processed to be substantially free of impurities or undesired solids, e.g., stems. The puree can then poured into a shallow vessel and quickly exposed to low temperature, i.e., flash frozen, for example at −20° C. or lower, preferably under a vacuum for removal of water content (lyophilization). The resultant plum extract can then be used in the compositions of the present invention. Alternatively, U.S. Publication No. 2005/0163880, which is incorporated by reference, describes an additional non-limiting method of preparing kakadu plum powder. In summary, the method includes: disintegrating kakadu plum fruit; treating the disintegrated kakadu plum material with enzymes to at least partially digest the material; juicing the kakadu plum material and drying the juice to produce a powder.

In other non-limiting aspects, the kakadu plum extract can further be enriched with ingredients that have beneficial properties for skin. Non-limiting examples of such ingredients include those listed throughout this specification, including for, example, antioxidants, vitamins, minerals, and amino acids. In certain aspects, enriching the kakadu plum can increase the ORAC value of the kakadu plum extract and/or the compositions of the present invention.

B. Acai Berry Extract

Acai berries can be obtained from a species of a palm tree (*Euterpe oleracea*) that grows in the Amazon rain forests of Brazil. The fruit is born in bunches of 3 to 8. The Acai berry contains vitamins, minerals, and essential fatty acids. This list includes vitamin B1, B2, and B3, vitamin C, vitamin E, iron, potassium, phosphorus, calcium, essential fatty acids Omega 6 and Omega 9, all the essential amino acids, flavonoids and protein. Flavonoids found in the acai berry include anthocyanins such as proanthrocyanadin, cyanidin-3-glucoside and cyanidin-3-rutinoside. Acai berries are also high in polyphenols. It has also been reported that acai berry has up to 33 times the antioxidant content as red wine grapes and has the highest ORAC value for any berry.

Acai berry extract is available commercially from a variety of companies, including, for example, Global Laboratories and NHS Labs Inc., Eagle, Idaho. Additionally, a person of ordinary skill in the art would be able to isolate acai berry extract from whole acai berry by using any suitable method known in the art. In one non-limiting example, acai berry can be disrupted by mechanical means which results in a puree. The puree is then processed to be substantially free of impurities or undesired solids, e.g., stems. The puree can then poured into a shallow vessel and quickly exposed to low temperature, i.e., flash frozen, for example at −20° C. or lower, preferably under a vacuum for removal of water content (lyophilization). The resultant berry extract can then be used in the compositions of the present invention.

In other non-limiting aspects, the acai berry extract can further be enriched with ingredients that have beneficial properties for skin. Non-limiting examples of such ingredients include those listed throughout this specification, including for, example, antioxidants, vitamins, minerals, and amino acids. In certain aspects, enriching the acai berry can increase the ORAC value of the acai berry extract and/or the compositions of the present invention.

C. Oxygen Radical Absorbance Capacity

Oxygen Radical Absorption (or Absorbance) Capacity (ORAC) is an assay that measures the antioxidant activity of an ingredient or composition. In essence, it can quantify the degree and length of time it takes to inhibit the action of an oxidizing agent such as oxygen radicals that are known to cause damage cells (e.g., skin cells). The ORAC value of the kakadu plum extract, acai berry extract and compositions of the present invention can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

D. Compositions of the Present Invention

A person of ordinary skill would recognize that the compositions of the present invention can include any number of combinations of ingredients (e.g., kakadu plum extract, acai berry extract, sun blocking agents, acute or chronic moisturizing agents (including, e.g., humectants, occlusive agents, and agents that affect the natural moisturization mechanisms of the skin), anti-oxidants, sunscreens having UVA and/or UVB protection, emollients, anti-irritants, vitamins, trace metals, anti-microbial agents, botanical extracts, fragrances, dyes and color ingredients, structuring agents, emulsifiers, etc.). Although certain concentration ranges of particular ingredients are indicated in other sections of the specification, it is also contemplated that in certain embodiments the concentrations of these and other ingredients can vary beyond those particular ranges. For example, in one-non-limiting aspect, a composition of the present invention can include at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

E. Vehicles

The compositions of the present invention can be incorporated into all types of vehicles. Non-limiting examples of suitable vehicles include emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that ingredients identified throughout this specification, including but not limited to kakadu plum extract and/or acai berry extract, can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. Nos. 6,387,398; 6,203,802; 5,411,744; Kreuter 1998).

F. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

G. Additional Compounds, Agents, and Ingredients that Can be Used in Combination With the Present Compositions Compositions of the present invention can include other beneficial agents and compounds such as, for example, sun blocking agents, acute or chronic moisturizing agents (including, e.g., humectants, occlusive agents, and agents that affect the natural moisturization mechanisms of the skin), anti-oxidants, sunscreens having UVA and/or UVB protection, emollients, anti-irritants, vitamins, trace metals, antimicrobial agents, botanical extracts, fragrances, dyes and color ingredients, structuring agents, and/or emulsifiers (see U.S. Pat. No. 6,290,938).

1. Sunblock Agents

Sunblock agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (and octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate), anthranilates, ethyl urocanate, homosalate, and Parsol 1789. Non-limiting examples of physical sunblocks include, kaolin, talc, petrolatum and metal oxides (e.g., titanium dioxide and zinc oxide).

2. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinalis extract, apricot (prunus armeniaca) kernel oil, arginine, arginine aspartate, arnica montana extract, aspartic acid, avocado (persea gratissima) oil, barrier sphingolipids, butyl alcohol, beeswax, behenyl alcohol, beta-sitosterol, birch (betula alba) bark extract, borage (borago officinalis) extract, butcherbroom (ruscus aculeatus) extract, butylene glycol, calendula officinalis extract, calendula officinalis oil, candelilla (euphorbia cerifera) wax, canola oil, caprylic/capric triglyceride, cardamon (elettaria cardamomum) oil, carnauba (copernicia cerifera) wax, carrot (daucus carota sativa) oil, castor (ricinus communis) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (anthemis nobilis) oil, cholesterol, cholesterol esters, cholesteryl hydroxystearate, citric acid, clary (salvia sclarea) oil, cocoa (theobroma cacao) butter, coco-caprylate/caprate, coconut (cocos nucifera) oil, collagen, collagen amino acids, corn (zea mays) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (oenothera biennis) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (vitis vinifera) seed oil, hazel (corylus americana) nut oil, hazel (corylus avellana) nut oil, hexylene glycol, hyaluronic acid, hybrid safflower (carthamus tinctorius) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (jasminum officinale) oil, jojoba (buxus chinensis) oil, kelp, kukui (aleurites moluccana) nut oil, lactamide MEA, laneth-16, laneth-10 acetate, lanolin, lanolin acid, lanolin alcohol, lanolin oil, lanolin wax, lavender (lavandula angustifolia) oil, lecithin, lemon (citrus medica limonum) oil, linoleic acid, linolenic acid, macadamia ternifolia nut oil, maltitol, matricaria (chamomilla recutita) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (olea europaea) oil, orange (citrus aurantium dulcis) oil, palm (elaeis guineensis) oil, palmitic acid, pantethine, panthenol, panthenyl ethyl ether, paraffin, PCA, peach (prunus persica) kernel oil, peanut (arachis hypogaea) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (mentha piperita) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (oryza sativa) bran oil, RNA, rosemary (rosmarinus officinalis) oil, rose oil, safflower (carthamus tinctorius) oil, sage (salvia officinalis) oil, sandalwood (santalum album) oil, serine, serum protein, sesame (sesamum indicum) oil, shea butter (butyrospermum parkii), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (helianthus annuus) seed oil, sweet almond (prunus amygdalus dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (triticum vulgare) germ oil, and ylang ylang (cananga odorata) oil.

3. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

4. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

5. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

6. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, poly silicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

7. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

8. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

9. Additional Compounds and Agents

Non-limiting examples of additional compounds and agents that can be used with the compositions of the present invention include, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), dyes and color ingredients (e.g. D&C blue no. 4, D&C green no. 5, D&C orange no. 4, D&C red no. 17, D&C red no. 33, D&C violet no. 2, D&C yellow no. 10, D&C yellow no. 11, etc.), emollients (i.e. organic esters, fatty acids, lanolin and its derivatives, plant and animal oils and fats, and di- and triglycerides), antimicrobial agents (e.g., triclosan and ethanol), and fragrances (natural and artificial).

H. Kits

The inventor also contemplates the use of a kits in certain aspects of the present invention. For example, any of the compositions, compounds, agents, or ingredients described in this specification may be included in a kit. In a non-limiting example, a kit can include a topical skin care composition that includes kakadu plum extract, acai berry extract, or a combination of both.

Containers of the kits can include a bottle, dispenser, package, compartment, or other types of containers, into which a component may be placed. The containers can dispense a pre-determined amount of the component (e.g. compositions of the present invention). The composition can be dispensed in a spray, an aerosol, or in a liquid form or semi-solid form. The containers can have spray, pump, or squeeze mechanisms. The container can include indicia on its surface. The indicia, for example, can be a word, a phrase, an abbreviation, a picture, or a symbol. The word or phrase can be "Mary Kay," "cosmetic," "sunscreen," etc.

Where there is more than one component in the kit (they may be packaged together), the kit also will generally contain a second, third or other additional containers into which the additional components may be separately placed. The kits of the present invention also can include a container housing the components in close confinement for commercial sale. Such containers may include injection or blow-molded plastic containers into which the desired bottles, dispensers, or packages are retained.

A kit can also include instructions for employing the kit components as well the use of any other compositions, compounds, agents, ingredients, or objects not included in the kit. Instructions may include variations that can be implemented. For example, the instructions can include an explanation of how to apply, use, and maintain the products or compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Kakadu Plum Extract Containing Compositions

Non-limiting examples of kakadu plum extract containing compositions of the present invention are described in Tables 1 and 2.

TABLE 1*

| Ingredient | % Concentration (by weight) |
|---|---|
| Phase A | |
| Water | 84.44 |
| Xanthum gum | 0.1 |
| M-paraben | 0.15 |
| P-paraben | 0.1 |
| Citric acid | 0.01 |

TABLE 1*-continued

| Ingredient | % Concentration (by weight) |
|---|---|
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Kakadu plum extract | 2.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.

TABLE 2*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Kakadu plum extract | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.

Derivatives and modifications of these ingredients can be used as substitutes. Additionally, other ingredients with similar physiological activities are contemplated as being useful as substitutes or as additional ingredients that can be used with the compositions of the present invention. It is also contemplated that the compositions of the present invention may include ingredients that do not substantially affect the efficacy of the compositions. Such ingredients can be used, for example, to vary the appearance, taste, and/or smell of the compositions of the present invention.

Example 2

Bioefficacy of Kakadu Plum Extract as an Anti-Oxidant

The ability of kakadu plum extract to act as an anti-oxidant was evaluted in terms of its ability to (1) reduce existing internal oxidation in cells; and (2) reduce external oxidative damage to cells.

Peroxide Assay: Cellular peroxides are measured flow cytometrically using the peroxide-specific dye, 2',7'-dichlorofluorescein diacetate (DCFH-DA). DCFH-DA is initially non-fluorescent and is rapidly concentrated within living cells by an enzyme-dependent process. Following modification by cellular peroxides, this dye exhibits an intense green fluorescence when excited by laser light. Basal peroxide production, generated by normal cellular metabolism, will induce a gradual development of low levels of peroxide-specific cellular fluorescence. As such, a measurement of this fluorescence without any treatment can act as a negative control for comparative purposes. Furthermore, extracellular peroxides (i.e., $H_2O_2$, added exogenously) can readily permeate the cell membrane and cause a rapid and dramatic increase in the peroxide-specific fluorescence of the cell. This assay can be used to characterize the effect of test articles on basal peroxide levels and/or the ability of extracellular peroxides to influence cellular peroxide levels. If the test article functions as an antioxidant, this assay can also be used to determine if the test article can permeate the cell membrane to quench intracellular peroxide or if it can only affect extracellular peroxide levels.

Human adult epidermal keratinocytes were cultured at 37° C. and 5.0% $CO_2$ in standard growth medium. At 70-80% confluent, cells were removed from plates using 0.025% Trypsin/EDTA. When the cells become rounded, the Trypsin/EDTA containing cells are removed from the culture dish and neutralized. Cells were centrifuged and the resulting pellet resuspended in media to generate a single cell suspension. Cellular peroxides were measured cytometrically by loading cultured keratinocytes with DCFH-DA (10 mM final conc.). Cells were treated with increasing concentrations of plant extract in triplicate followed with or without exogenous addition of hydrogen peroxide (60 mM). The level of induced or un-induced cellular peroxide was analyzed. To confirm that antioxidant activity of the cells could be adduced, positive controls for an antioxidant response using Trolox™ (an analog of vitamin E and a known antioxidant) were employed. The peroxide-specific fluorescence of the cells was measured using a flow cytometer and the Mean Fluorescence Intensity (MFI). Debris was excluded from analysis using a gate created on a dual-parameter light scattergram. These experiments were repeated in triplicate, and the percent reduction of oxidative damage compared to untreated control was calculated (FIG. 1). Kakadu plum extract reduced oxidative damage from external insults.

Example 3

Collagen Production in Human Fibroblast Dermal Cells in the Presence of Kakadu Plum Extract The ability of kakadu plum extract to increase collagen production in human fibroblast dermal cells was studied.

Figure 2:
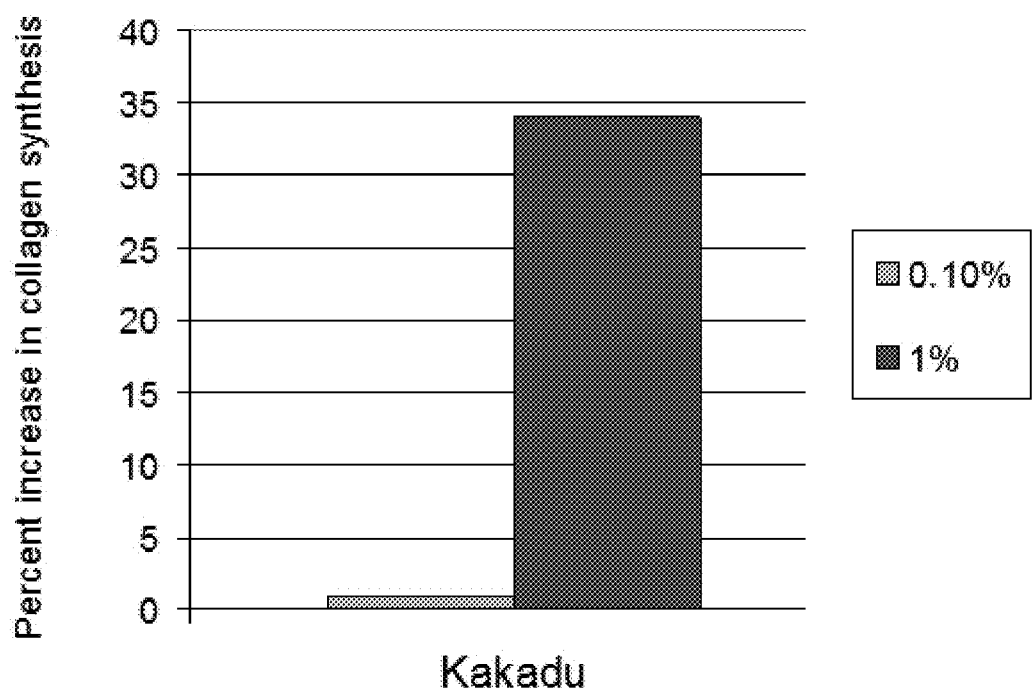
FIG. 2. Collagen production in dermal cells as influenced by exposure to kakadu plum extract. Similar to FIG. 1, the original liquid extract is listed at 20-30% W/W with 10-20% denatured alcohol and >50% 1,3 butylene glycol. A 10% stock of this extract was prepared by dilution is water (2-3% fruit extract) which was further diluted in the assay to 1.0% and 0.1% (0.2-0.3% and 0.02-0.03% kakadu fruit extract, based upon the amount in the original extract).

Collagen production protocol: Normal human dermal fibroblast (NHDF) cells were grown to subconfluence from a frozen vial in tissue culture flasks (T25's). Two confluent T25's were trypsinized, washed, resuspended to 16 mls and seeded heavily into a 96 well plate (200 µl/well) (Columns 4-12 only). Cells were allowed to grow overnight or until the cells reached 100% confluence. Upon reaching confluence, the spent media was aspirated and 200 µl of fresh media with or without samples of interest (in triplicate) were added. The liquid extract in FIG. 2 is 1.0% (20 µl of 100× stock) and 0.1% (2 µl of 100× stock) kakadu extract and was diluted into a final volume of 200 µl NHDF growth medium (note that the liquid extract is listed at 20-30% W/W with 10-20% denatured alcohol and >50% 1,3 butylene glycol. A 10% stock of this extract was prepared by dilution is water (2-3% fruit extract) which was further diluted in the assay to 1.0% and 0.1% (0.2-0.3% and 0.02-0.03% kakadu fruit extract, based upon the amount in the original extract). One set of cells was treated with L-ascorbic acid (vitamin C), an agent known to increase collagen production, at a final concentration of 18 µg/ml in triplicate as a positive control. Cells were incubated for 3 days in the presence of the samples at 37° C./5% $CO_2$. Supernatants were harvested and frozen at −80° C. until assayed with the Procollagen Peptide (PIP) kit (Takara Bio Inc.), designed to measure procollagen peptide in the range of 40 to 640 ng/ml. The cells in this system can be expected to produce at least 3000 ng/ml of procollagen peptide (media control). Tissue culture supernatants need to be diluted 1:100 with the sample diluent included in the kit. The protocol supplied with the kit was followed. Brief instructions are provided:

Allow plate to reach room temperature before opening the foil package. Allow the supernatants to thaw to room temp. slowly.

Add 1 ml $dH_2O$ to Vial 3: PIP Standard—Mix gently and allow to stand at room temp. for 10 min. prior to use.

Add 11 ml $H_2O$ to Vial 2: Antibody-POD Conjugate—Mix gently and allow to stand at room temp. for 10 min. prior to use.

Prepare Standard curve as directed in protocol booklet.

Dilute all supernatants 1:40 with sample diluent (supplied with kit).

Transfer 100 µl of POD conjugate/well with a multichannel pipet. Subsequently add 20 µl of diluted standard or sample/well in triplicate.

Incubate (covered) for 3 hours at 37° C.

Wash plate 4 times with 400 µl of wash solution (see protocol booklet for complete washing instructions).

Add 100 µl substrate solution/well and incubate at room temp for 15 min.

Add 100 µl stop solution/well. Tap plate gently to mix.

Measure absorbance at 450 nm with a plate reader within 1 hour.

The standard curve is plotted using a 4 parameter curve fit. The concentration of the procollagen peptide was determined from the standard curve. The results from the standard curve must be multiplied by the dilution factor to yield the total number of ng/ml of the procollagen peptide.

Collagen production in dermal cells in the presence of 1% kakadu plum extract increased significantly compared to untreated control dermal cells (FIG. 2).

Example 4

Reducing Inflammation in Human Epidermal Keratinocytes Using Kakadu Plum Extract The ability of kakadu plum extract to reduce inflammation in human epidermal keratinocytes was studied using a cytokine array assay.

Cytokine array: Human epidermal keratinocytes were cultured to 70-80% confluency. The media in the plate was aspirated and 0.025% trypsin/EDTA was added. When the cells became rounded, the culture dish was gently tapped to release the cells. The trypsin/EDTA containing cells were removed from the culture dish and neutralized. Cells were centrifuged for 5 min. at 180×g. The cells formed a pellet and the supernatant was aspirated. The resulting pellet was resuspended in EpiLife™ media (Cascade Biologics). The cells were seeded in 6-well plates at approximately 10-20% confluency. After the cells became approximately 80% confluent, the media was aspirated and 1.0 ml of EpiLife™, along with phorbol 13-Myristate 12-acetate ("PMA") (a known inducer of inflammation) and the test article dilution were added to two replicate wells (i.e., 1.0% (100 µl of 100× stock) and 0.1% (10 µl of 100× stock) kakadu extract as prepared in FIG. 2 was diluted into a final volume of 1 ml EpiLife Growth Medium). The media was gently swirled to ensure adequate mixing. In addition, 1.0 ml of EpiLife™ was added to the control wells, with and without additional PMA. The plates were then incubated at 37±1° C. and 5.0±1% $CO_2$ for approximately 5 hours after dosing. Following this 5-hour incubation, all media was collected in conical tubes and frozen at −70° C. and the frozen media was subsequently shipped to the sponsor on dry ice. 16-pad FAST slides arrayed in triplicate with 16 anti-cytokine antibodies plus experimental controls were purchased from Whatman BioSciences.

On the day of the analysis, a 16-pad hybridization chamber was attached to the slides, and the slides were placed into a FASTFrame (4 slides per frame) for processing. Arrays were blocked for 15 min. at room temp. using 70 ml S&S Protein Array Blocking buffer (Whatman Schleicher and Scheull). Blocking buffer was removed and 70 ml of each supernatant sample was added to each array. Arrays were incubated for 3 hours at room temp. with gentle agitation. Arrays were washed 3 times with TBS-T. Arrays were treated with 70 ml of an antibody cocktail, containing one biotinylated antibody corresponding to each of the arrayed capture antibodies. Arrays were incubated for 1 hour at room temp. with gentle agitation. Arrays were washed 3 times with TBS-T. Arrays were incubated with 70 ml of a solution containing streptavidin-Cy5 conjugate for 1 hour at room temp. with gentle agitation. Arrays were washed 3 times with TBS-T, quickly rinsed in de-ionized water, and dried.

Slides were imaged in a Perkin-Elmer ScanArray 4000 confocal fluorescent imaging system. Array images were saved as 16-bit TIF files, with 10 micron pixel resolution. Images were analyzed using Imaging Research ArrayVision software. Briefly, spot intensities were determined by subtracting background signal. Spot replicates from each sample condition were averaged and then compared to the appropriate controls. Microsoft Excel and GraphPad Prism were used for additional analysis and data presentation.

Figure 3:
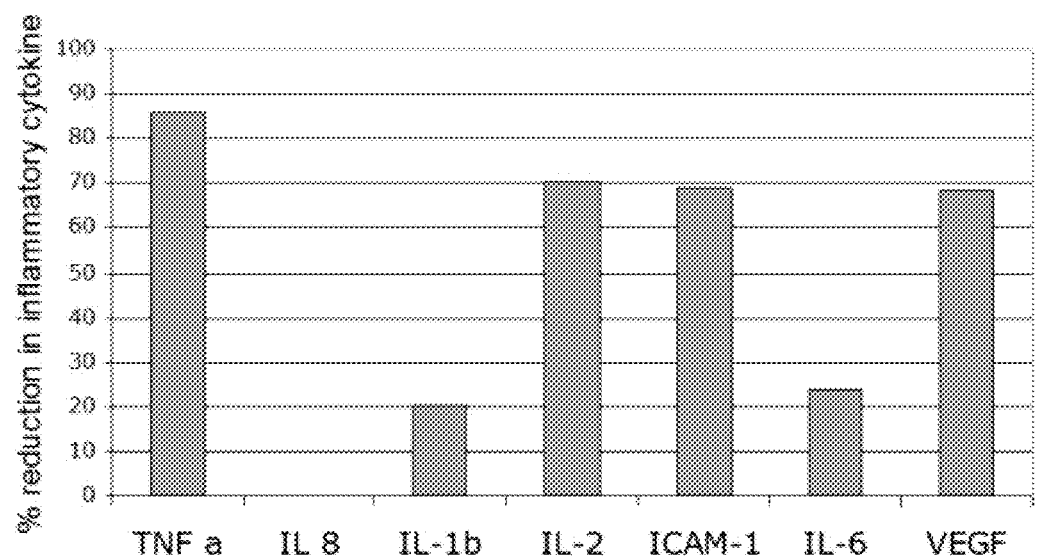
FIG. 3. Inflammatory profile regarding human epidermal keratinocytes exposed to kakadu plum extract.
Figure 4:
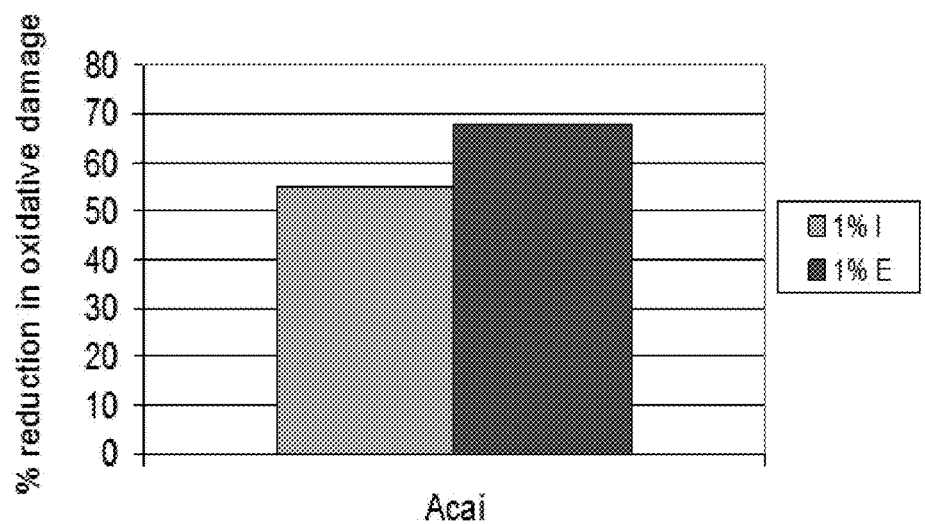
FIG. 4. Anti-oxidant effects of acai berry extract with respect to human epidermal keratinocytes. E stands for external antioxidant according to the assay (External meaning is able to reduce oxidation that is introduced exogenously). I stands for Internal which concerns the ability to reduce endogenous oxidation, which is a result of metabolism in the cell. The original powder extract is 20-30% W/W with 70-80% carrier protein. The original dry powder extract was weighed at 100 mg/ml w/v with 50:50 mix of water and 90% denatured alcohol to create a 100× stock. For the assay, the resulting 100× stock was prepared by dilution in water to 1.0% and 0.1% (1.0 mg/ml and 0.1 mg/ml).

The percent reduction in certain inflammatory cytokines can be seen in FIG. 3. While kakadu plum extract reduced the inflammatory response associated with several types of cytokines, the extract is particularly effective at reducing the inflammatory responses of IL-8 and IL-6. In this manner, then, the reduction in inflammatory responses as seen with kakadu plum extract and acai berry extract are complementary (see FIG. 7).

Example 5

Non-Limiting Examples of Acai Berry Extract Containing Compositions of the Present Invention Non-limiting examples of kakadu plum extract containing compositions of the present invention are described in Tables 3 and 4.

TABLE 3*

| Ingredient | % Concentration (by weight) |
| --- | --- |
| Phase A | |
| Water | 84.44 |
| Xanthum gum | 0.1 |
| M-paraben | 0.15 |
| P-paraben | 0.1 |
| Citric acid | 0.01 |

TABLE 3*-continued

| Ingredient | % Concentration (by weight) |
|---|---|
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Acai berry extract | 2.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.

TABLE 4*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Acai berry extract | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.

Example 6

Bioefficacy of Acai Berry Extract: Action as an Anti-Oxidant

The ability of acai berry extract to act as an anti-oxidant was evaluted in terms of its ability to (1) reduce existing internal oxidation in cells; and (2) reduce external oxidative damage to cells. The Peroxide Assay described in Example 2 was used, wherein $H_2O_2$, DCFH-DA dye and acai berry extract (in place of kakadu plum extract) were used in the same amounts.

Figure 5:
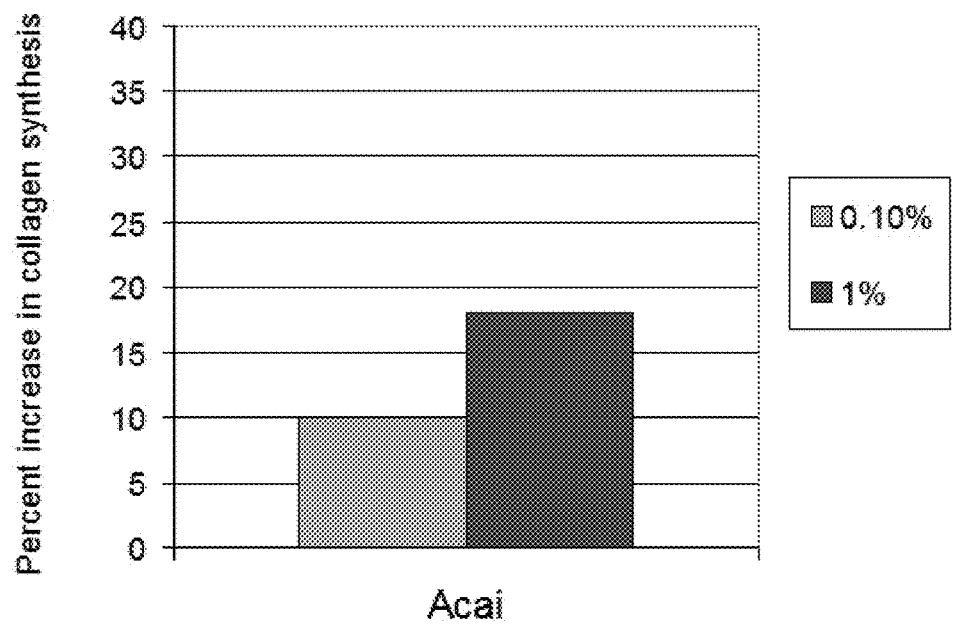
FIG. 5. Study of collagen production in dermal cells as influenced by exposure to acai berry extract. The original powder extract is 20-30% W/W with 70-80% carrier protein. The original dry powder extract was weighed at 100 mg/ml w/v with 50:50 mix of water and 90% denatured alcohol to create a 100× stock. For the assay, the resulting 100× stock was prepared by dilution in water to 1.0% and 0.1% (1.0 mg/ml and 0.1 mg/ml).

These experiments were repeated in triplicate, and the percent reduction of oxidative damage was calculated (FIG. 5). Acai berry extract reduces oxidative damage from both internal and external insults.

Example 7

Collagen Production in Human Fibroblast Dermal Cells in the Presence of Acai Berry Extract The ability of acai berry extract to increase collagen production in human fibroblast dermal cells was studied. The collagen production protocol as described in Example 3 was employed, utilizing the same amount of acai berry extract in place of the kakadu plum extract.

Collagen production in dermal cells in the presence of 1% acai berry extract increased significantly compared to control dermal cells (FIG. 6), but less than the percent collagen produced in the presence of the same amount of kakadu plum extract as shown in FIG. 2.

Example 8

Reducing Inflammation in Human Epidermal Keratinocytes Using Acai Berry Extract

The ability of acai berry extract to reduce inflammation in human epidermal keratinocytes was studied using a cytokine array assay. The cytokine assay of Example 4 was employed, using acai berry extract in place of kakadu plum extract.

Figure 6:
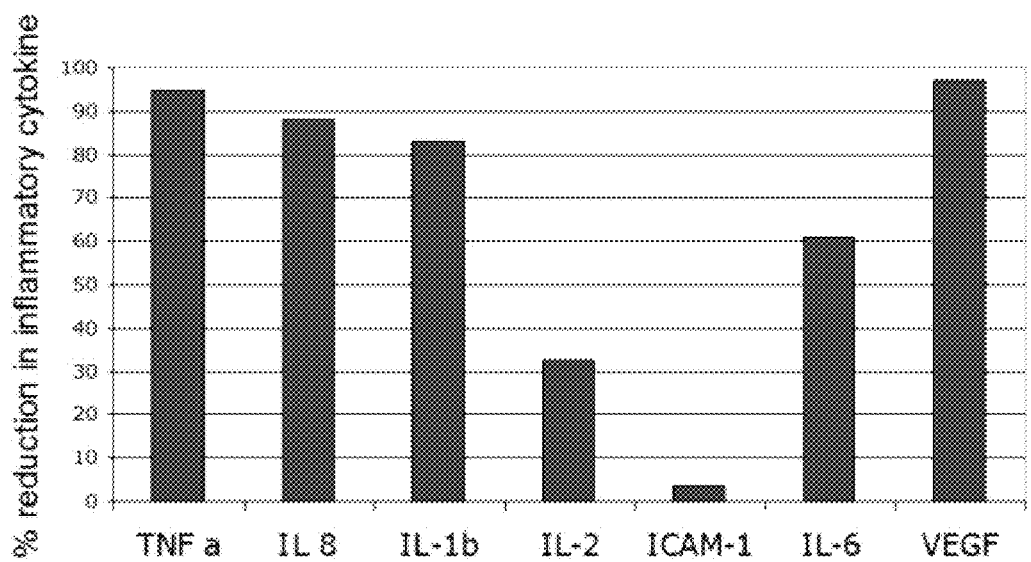
FIG. 6. Inflammatory profile regarding human epidermal keratinocytes exposed to acai berry extract.
Figure 7:
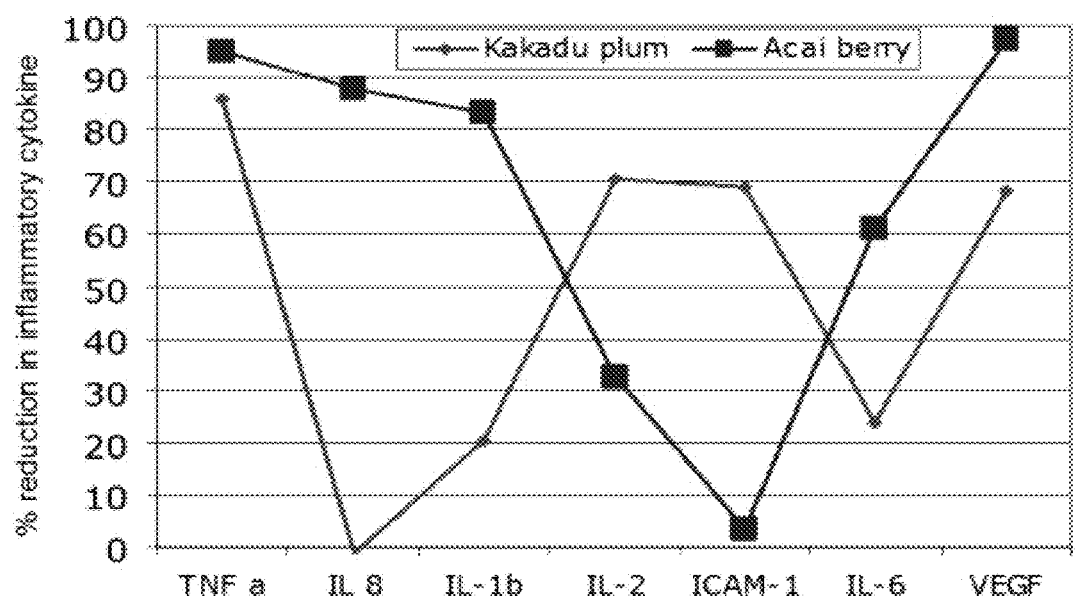
FIG. 7. Complementary inflammatory response profiles of kakadu plum extract and acai berry extract.

The percent reduction of certain inflammatory cytokines can be seen in FIG. 6. While acai berry extract reduced the inflammatory response associated with several types of cytokines, the extract is particularly effective at reducing the inflammatory responses of IL-2 and ICAM-6. the reduction in inflammatory responses as seen with kakadu plum extract and acai berry extract are complementary (FIG. 7).

Example 9

Non-Limiting Examples of Compositions of the Present Invention Comprising Kakadu Plum Extract and Acai Berry Extract Non-limiting examples of kakadu plum extract containing compositions of the present invention are described in Tables 5 and 6.

TABLE 5*

| Ingredient | % Concentration (by weight) |
|---|---|
| Phase A | |
| Water | 84.44 |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Kakadu plum extract | 1.0 |
| Acai berry extract | 1.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.

TABLE 6*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |

TABLE 6*-continued

| Ingredient | % Concentration (by weight) |
| --- | --- |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Kakadu plum extract | 1.0 |
| Acai berry extract | 1.0 |

*Add ingredients in phase A to beaker and heat to 70-75° C. while mixing. Subsequently, add the phase B ingredient with phase A and cool to 30° C. with mixing. Subsequently, add phase C ingredient while mixing.

Example 10

Determining Efficacy of the Compositions of the Present Invention

The efficacy of compositions of the present inventions can be determined by methods known to those of ordinary skill in the art. The following are non-limiting procedures that can be used in the context of the present invention. It should be recognized that other testing procedures can be used, including, for example, objective and subjective procedures.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72 C). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 2,798,053
U.S. Pat. No. 3,755,560
U.S. Pat. No. 4,421,769
U.S. Pat. No. 4,509,949
U.S. Pat. No. 4,599,379
U.S. Pat. No. 4,628,078
U.S. Pat. No. 4,835,206
U.S. Pat. No. 4,849,484
U.S. Pat. No. 5,011,681
U.S. Pat. No. 5,087,445
U.S. Pat. No. 5,100,660
U.S. Pat. No. 5,411,744
U.S. Pat. No. 5,720,963
U.S. Pat. No. 6,203,802
U.S. Pat. No. 6,290,938
U.S. Pat. No. 6,387,398
U.S. Pat. No. 6,495,126
U.S. Publn. 2004/0109905
U.S. Publn. 2005/0163880
U.S. Prov. App. 60/760,103
U.S. Prov. App. 60/760,977
U.S. Prov. App. 60/760,979
Cao et al., *Free Radic. Biol. Med.,* 14:303-311, 1993.
CTFA International Cosmetic Ingredient Dictionary, Fourth edition, pps. 12 and 80, 1991.
J. Kreuter, *J. Microencapsulation,* 5:115-127 (1988).
McCutcheon's, Detergents and Emulsifiers, North American Edition (1986).
Packman and Gams, *J. Soc. Cos. Chem.,* 29:70-90, 1978.
Remington's Pharmaceutical Sciences, 18th Ed. Mack Printing Company, 1289-1329, 1990.
Schiltz et al. *J. Investigative Dermatology,* 87:663-667, 1986.

The invention claimed is:

1. A method of reducing TNF-α production in human epidermal keratinocytes, the method comprising topically applying to skin in need thereof a composition comprising:
   an effective amount of a liquid kakadu plum extract comprising kakadu plum fruit, alcohol, and butylene glycol to reduce TNF-α production in human epidermal keratinocytes of the skin; and
   an effective amount of a liquid acai berry extract comprising acai berry fruit, water, and alcohol to reduce TNF-α production in human epidermal keratinocytes of the skin, wherein the composition comprises 0.05% to 5%, by weight, of the kakadu plum extract and 0.05% to 5%, by weight, of the acai berry extract.

2. The method of claim 1, wherein the skin in need thereof is inflamed skin.

3. The method of claim 1, wherein the composition is an emulsion.

4. The method of claim 3, wherein the emulsion is an oil-in-water emulsion.

5. The method of claim 1, wherein the composition is a cream or a lotion.

6. The method of claim 1, wherein the composition comprises 0.05% to 1%, by weight, of the kakadu plum extract and 0.05% to 1%, by weight, of the acai berry extract.

* * * * *